(12) United States Patent
Konya et al.

(10) Patent No.: US 9,364,172 B2
(45) Date of Patent: Jun. 14, 2016

(54) SYSTEM FOR COLLECTING SAMPLES AND METHOD FOR COLLECTING A LIQUID SAMPLE

(75) Inventors: Ahmet Konya, Waldsee (DE); Frank Deck, Niederkirchen (DE); Karl-Peter Ebert, Fränkisch-Crumbach (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 1583 days.

(21) Appl. No.: 12/422,021

(22) Filed: Apr. 10, 2009

(65) Prior Publication Data
US 2009/0270763 A1 Oct. 29, 2009

Related U.S. Application Data

(63) Continuation of application No. PCT/EP2007/060759, filed on Oct. 10, 2007.

(30) Foreign Application Priority Data

Oct. 12, 2006 (EP) ..................................... 06122214

(51) Int. Cl.
*A61B 5/15* (2006.01)
*A61B 5/145* (2006.01)
*A61B 5/151* (2006.01)

(52) U.S. Cl.
CPC ........... *A61B 5/1411* (2013.01); *A61B 5/14532* (2013.01); *A61B 5/15146* (2013.01)

(58) Field of Classification Search
CPC ........... A61B 5/14532; A61B 5/15146; A61B 5/1411
USPC ........... 600/567, 583, 562, 564; 606/181, 182
See application file for complete search history.

(56) References Cited

U.S. PATENT DOCUMENTS

| 4,442,836 A | 4/1984 | Meinecke et al. |
|---|---|---|
| 4,924,879 A | 5/1990 | O'Brien |

(Continued)

FOREIGN PATENT DOCUMENTS

| CA | 2311496 A1 | 6/2009 |
|---|---|---|
| DE | 103 43 896 A1 | 4/2005 |

(Continued)

OTHER PUBLICATIONS

English Translation of the International Preliminary Report on Patentability (IPRP).

(Continued)

*Primary Examiner* — Adam J Eiseman
*Assistant Examiner* — Patrick Fernandes
(74) *Attorney, Agent, or Firm* — Bose McKinney & Evans LLP (57) ABSTRACT

The invention relates to a system for collecting samples and to a method for collecting a liquid sample. The system comprises at least one analytical aid, the analytical aid comprising a lancet and a test element, and the test element having a test field for analysis of the liquid sample. The system for collecting samples comprises a coupling element which can be successively connected to the lancet, in a first position of the analytical aid, and to the test element, in a second position of the analytical aid. The system for collecting samples also comprises a drive unit for moving the coupling element from a rest position to a deployed position, such that the movement of the coupling element is transmitted to the lancet, coupled thereto, in order to execute a puncturing movement, or is transmitted to the test element, coupled thereto, in order to execute a sample recovery movement.

30 Claims, 6 Drawing Sheets

(56) References Cited

U.S. PATENT DOCUMENTS

| | | |
|---|---|---|
| 5,554,166 A | 9/1996 | Lange et al. |
| 5,846,837 A | 12/1998 | Thym et al. |
| 6,036,919 A | 3/2000 | Thym et al. |
| 7,780,631 B2 * | 8/2010 | Lum ........................ A61B 5/053 604/117 |
| 7,833,172 B2 * | 11/2010 | Hein et al. .................... 600/583 |
| 7,909,776 B2 * | 3/2011 | Roe et al. ...................... 600/583 |
| 2002/0188224 A1 * | 12/2002 | Roe ...................... A61B 5/1411 600/584 |
| 2003/0212345 A1 * | 11/2003 | McAllister et al. ........... 600/584 |
| 2004/0127928 A1 | 7/2004 | Whitson et al. |
| 2005/0245845 A1 * | 11/2005 | Roe ................... A61B 5/15146 600/583 |
| 2005/0288637 A1 | 12/2005 | Kuhr et al. |
| 2006/0002816 A1 | 1/2006 | Zimmer et al. |
| 2006/0155317 A1 * | 7/2006 | List ............................... 606/181 |
| 2006/0173380 A1 | 8/2006 | Hoenes et al. |
| 2006/0216817 A1 | 9/2006 | Hoenes et al. |
| 2007/0219572 A1 | 9/2007 | Deck et al. |
| 2008/0269791 A1 * | 10/2008 | Hoenes ................ A61B 5/1411 606/181 |
| 2009/0326355 A1 * | 12/2009 | Brenneman et al. .......... 600/347 |

FOREIGN PATENT DOCUMENTS

| | | |
|---|---|---|
| DE | 103 32 488 A1 | 5/2005 |
| EP | 1 424 040 A1 | 6/2004 |
| WO | WO 97/02487 A1 | 1/1997 |
| WO | WO 98/48695 A1 | 11/1998 |
| WO | WO 2004/056269 A1 | 7/2004 |
| WO | WO 2005/107596 A2 | 11/2005 |
| WO | WO 2006/013045 A1 | 2/2006 |

OTHER PUBLICATIONS

International Search Report (ISR) Dated Jan. 8, 2009.

* cited by examiner

SYSTEM FOR COLLECTING SAMPLES AND METHOD FOR COLLECTING A LIQUID SAMPLE

RELATED APPLICATIONS

This application is a continuation application of International Application PCT/EP2007/060759, filed Oct. 10, 2007, which claims priority to EP 06122214.7, filed Oct. 12, 2006, which are hereby incorporated by reference in their entirety.

BACKGROUND

The invention relates to a system for collecting samples and to a method for collecting a liquid sample, in particular, of a body fluid such as blood or interstitial fluid. The sample collection procedure involves the steps of creating a perforation in the skin by insertion of a lancet, such that the sample fluid emerges from the perforation, and of recovering the sample on a test element on which said sample can be analyzed in a test field.

In clinical diagnostics, examination of blood samples or of interstitial fluid permits early and reliable detection of pathological conditions and also specific and reliable monitoring of physical states. Medical diagnostics entails collecting a sample of blood or of interstitial fluid from the individual who is to be examined.

To collect the sample, the skin of the person to be examined can be punctured, for example, at the finger pad or ear lobe, with the aid of a sterile, sharp lancet, in order to obtain a few microliters of blood for analysis. This method is particularly suitable for sample analysis that is carried out directly after the sample has been collected.

In the area of home monitoring in particular, in other words, where persons without specialized medical training carry out simple analyses of blood or of interstitial fluid themselves, and particularly for diabetics taking blood samples on a regular basis, several times a day, to monitor their blood glucose concentration, lancets and associated devices (puncturing aids) are sold that allow samples to be taken with the least possible discomfort and in a reproducible manner. Such lancets and devices (puncturing aids) are the subject matter of, for example, WO-A 98/48695, U.S. Pat. No. 4,442,836, U.S. Pat. No. 5,554,166 or WO 2006/013045.

Self-monitoring of blood glucose levels is a method of diabetes control that is nowadays applied worldwide. Blood glucose monitors in the prior art comprise an analysis device into which a test element (test strip) is inserted. The test element is brought into contact with a droplet of a sample which has previously been collected by means of a puncturing aid, for example from the pad of a finger.

Samples of fluids, for example, body fluids such as blood or urine, are frequently analyzed using analysis appliances in which the sample to be analyzed is located on a test field of a test element and may react with one or more reagents in the test field before it is analyzed. Optical, in particular photometric, evaluation and electrochemical evaluation of test elements represent the most common methods for rapid determination of the concentration of analytes in samples. Analysis systems with test elements for sample analysis are generally used in the field of analysis, environmental analysis and in particular in the field of medical diagnostics. Test elements that are evaluated photometrically or electrochemically are of great value, particularly in blood glucose diagnosis from capillary blood.

There are various forms of test elements. By way of example, substantially square plates are known, which are also referred to as slides, in whose center a multilayer test field is located. Diagnostic test elements which are in the form of strips are referred to as test strips. The prior art extensively describes test elements, for example, in documents CA 2311496, U.S. Pat. No. 5,846,837, U.S. Pat. No. 6,036,919 or WO 97/02487.

Other multilayer test elements known in the prior art are analysis tapes comprising a multiplicity of test fields, which are wound up in a cassette and made available for use in an analysis appliance. Such cassettes and analysis tapes are described, for example, in documents DE 103 32 488, DE 103 43 896, EP 1 424 040, WO 2004/056269 and US 2006/0002816.

The numerous system components (lancet, puncturing aid, test element and analysis appliance) require a lot of space and involve complex handling. Systems have also been developed which have a greater degree of integration and are thus easier to handle and in which, for example, the test elements are stored in the analysis appliance and made available for the measurement. A further step in terms of miniaturization can be achieved, for example, by integrating several functions or function elements within a single analytical aid that is disposable. For example, the operating sequence can be greatly simplified by a suitable combination of the puncturing procedure and of the detection of the analyte concentration by means of a sensor on a test element.

U.S. Publication No. 2006/0155317 discloses a lancet device for generating a puncture wound in a skin surface, which device comprises an integrated test element in the form of a reference element with a lancet and a sample-collecting unit. The test element is coupled securely to a coupling mechanism of the lancet device. In a first position of the coupling mechanism, the lancet of the test element is actuated by means of a coupling rod and connecting rod, and a puncturing movement is carried out. By means of a pivoting movement, the entire coupling mechanism, together with the test element coupled securely thereon, is then moved to a second position in which an opening of a sample recovery channel of the test element lies over the puncture site in order to recover a liquid sample.

This concept known from U.S. Publication No. 2006/0155317 is relatively complex, since the combination of several vertical movements of the coupling mechanism and the required pivoting movements of the coupling mechanism (in each case with the test element coupled securely thereon), and the separate drive mechanism required for the lancet movement involve considerable outlay in terms of construction. Moreover, the concept illustrated therein can be technically expanded on only with difficulty, by means of a multiplicity of test elements (for example from a magazine) being used one after another in an automated manner.

WO 2005/107596 discloses a multiplicity of lancets arranged spaced apart from one another on a tape. According to one embodiment, the tape not only carries the lancets, but also a multiplicity of test elements, which are each assigned to one of the lancets. This is therefore a tape with a multiplicity of analytical aids which are arranged spaced apart from one another and which permit the integration of puncturing procedures and sample recovery procedures within one sample-collecting system.

SUMMARY

The present invention provides a system for collecting samples and a method for collecting a liquid sample, which system and method integrate the functions of insertion of the lancet of an analytical aid into the skin and recovery of the liquid sample on a test element of the analytical aid. The present invention achieves a high degree of integration and a small overall size of a system for collecting samples.

The system for collecting samples comprises at least one analytical aid, the analytical aid comprising a lancet and a test element, and the test element having a test field for analysis of the liquid sample. The system for collecting samples comprises a coupling element, which can be successively connected to the lancet in a first position of the analytical aid and to the test element in a second position of the analytical aid. The system for collecting samples also comprises a drive unit designed to move the coupling element from a rest position to a deployed position, such that the movement of the coupling element is transmitted to the lancet, coupled thereto, in order to execute a puncturing movement, or is transmitted to the test element, coupled thereto, in order to execute a sample recovery movement.

In this context, an analytical aid is a means that combines the two functions of inserting a lancet into the skin and recovering a sample, in particular, the three functions of inserting a lancet into the skin, recovering a sample, and making available test chemicals for analysis of the sample. The analytical aid used for the present invention comprises a lancet and a test element. The test element has a test field for analysis of the liquid sample. In this context, a test field is a limited area of the test element where the liquid sample is located while it is being analyzed, e.g., electrochemically or photometrically. The test field can comprise a detection chemical that reacts with the sample and thus has an effect (e.g. a color change) that is detectable in the analysis, in particular as a function of the concentration of an analyte in the sample. In such a test field, for example, it is possible to analyze the concentration of glucose in a body fluid such as blood or interstitial fluid.

Use can be made, for example, of individual strip-shaped analytical aids or of a multiplicity of analytical aids arranged on a tape. The possibility of using not just one individual analytical aid, but a multiplicity of such aids, represents a considerable advantage of the system according to the invention for collecting samples in relation to known systems, for example the system known from U.S. Publication No. 2006/0155317.

According to one exemplary embodiment of the present invention, for example, a multiplicity of analytical aids on an analysis tape are used. Alternatively, however, the system for collecting samples can also be designed differently for use with a multiplicity of analytical aids. Thus, for example, a multiplicity of analytical aids can be received on a transport tape. In this context, the term transport tape is interpreted broadly and can include almost any desired mechanical connection between adjacent analytical aids or a support on which the lancets and test elements are arranged, for example, a link chain, a film connection or some other type of connection. Alternatively, the analytical aids can also be held in a magazine, for example, a bar magazine, a stack magazine, a drum magazine or a zigzag magazine. Moreover, the analytical aids can also be held on a test element disk, for example, a round test element disk. Such test element disks are known in principle and can, for example, have a plastic support, a paper support or a ceramic support, for example, with lancets and test elements arranged in the area of an outer edge, for example, in the form of test chemical fields. For example, lancets and test chemical fields can be arranged in alternating sequence around the periphery of a test element disk which is successively rotated in stages relative to the coupling element, such that a lancet can be coupled in a first position and a test chemical field in a second position. Other technical configurations, however, are also possible for the use of a multiplicity of analytical aids.

The exemplary system for collecting samples comprises a coupling element which can be successively connected to the lancet in a first position of the analytical aid and to the test element in a second position of the analytical aid. For this purpose, the analytical aid can be transported automatically or manually from the first position to the second position. For automatic transport, the system typically comprises a transport device for transporting the analytical aid from the first position to the second position relative to the coupling element arranged in the rest position. If the analytical aid is arranged on an analysis tape which is rolled up on reels in a cassette, such a transport device, e.g., a reel for rolling up the analysis tape, can rotate about a defined angle of rotation until the next test element or the next lancet is located in the desired position relative to the coupling element.

In exemplary embodiments, the coupling element is successively connected in the first position to the lancet and in the second position to the test element. In this way, the system according to the invention for collecting samples differs from known systems for collecting samples, for example from the system which is disclosed in U.S. Publication No. 2006/0155317 and in which there is a fixed initial connection between coupling element and test element, which connection is then maintained, and the relative position between coupling element and test element is no longer changed.

In particular, this connection procedure can be such that, first of all, one and the same coupling element is connected in the first position to the lancet and a puncturing movement can then take place, after which the coupling element is once again disconnected. A movement to the second position takes place, and then the coupling element is connected to the test element, after which a sample recovery movement by the test element can take place. The coupling element can then be disconnected again from the test element. Thus, the same coupling element is preferably used for connection to the lancet and to the test element.

When the coupling element is connected to the lancet, its defined movement from a rest position (non-deployed position) to its deployed position has the effect that the lancet likewise executes a movement, namely, a puncturing movement. When the coupling element is connected to the test element, its defined movement from the rest position to the deployed position has the effect that the test element likewise executes a movement, namely, a sample recovery movement. In this way too, the system according to the invention for collecting samples differs from known systems for collecting samples, for example from the system which is disclosed in U.S. Publication No. 2006/0155317 and in which, although the entire coupling element is deployed for the subsequent collection of the sample, the lancet is not driven by a movement of the coupling element, but by the movement of a connecting rod separate from the coupling element.

In exemplary embodiments, the lancet or the test element can be connected to the coupling element in any desired manner which is known to a person skilled in the art and which ensures that a movement of the coupling element from its rest position to its deployed position leads to a puncturing movement of the lancet or to a sample recovery movement of the test element. If several analytical aids, i.e., several lancets and test elements, are arranged on a common support, for example, on an analysis tape or support tape, the deployment in both cases (i.e., the deployment of the lancet in the first position and/or the deployment of the test element in the second position) can take place in such a way that the support is also deployed, so that the local positioning of the lancet or of the test element relative to the support does not change, or changes only slightly, or the lancet or the test element can be deployed in such a way that the support remains substantially at rest and only the lancet or the test element is deployed. Of course, the deployed positions for the lancet and for the test element can also differ. For example, for a puncturing movement of the lancet, the deployment movements (e.g., depths of insertion) can be different than those for a sample recovery movement of the test element, in which only slight deployment movements are necessary. The deployment movements can also differ in terms of their speeds, for example.

The connection can be made directly or indirectly via other component parts. For example, the coupling element can grip around the analytical aid at the respective position and, in its movement to the deployed position, lift the analytical aid by a defined distance.

An active connection can be understood as a connection in which the coupling element is connected to the analytical aid (for example, by a force-fit and/or form-fit connection, for example, by gripping of the lancet or of the test element or by a microstructure with barbs which, when the coupling element is drawn back, also draw back the lancet or test element) in such a way that the return movement of the lancet or of the test element from the deployed position to the rest position is guided and driven too by the coupling element. In general, a gripper with a particular surface structure or a gripper surface made of a suitable material can be used for connection to the analytical aid. In the case of a passive connection, by contrast, the coupling element pushes the analytical aid, for example, the lancet or test element, into the deployed position. The return movement of the analytical aid to its rest position should then be effected by an additional drive element, for example, by a spring which is tensioned upon deployment of the lancet or of the test element and, when it relaxes, acts on the lancet or the test element so as to effect a return movement of the lancet or of the test element to the rest position. This spring can, for example, also be a component part of the test element itself, for example a support tape of the test element, which exerts a spring action by virtue of its inherent stress.

The system for collecting samples also comprises a drive unit which drives a movement of the coupling element from the rest position to the deployed position. The drive unit in particular provides the energy for moving the coupling element and represents the means for transmitting the energy to the coupling element.

The movement of the coupling element from the rest position to the deployed position and back again to the rest position is driven by the drive unit and is transmitted to the lancet, coupled thereto, in order to execute a puncturing movement, or is transmitted to the test element, coupled thereto, in order to execute a sample recovery movement.

In this context, the puncturing movement is a guided movement in which the lancet is moved forward and then back again by a defined distance. The tip of the lancet can, for example, emerge by a defined length from an opening in a housing of the system according to the invention for collecting samples, said length defining the puncture depth, and can penetrate, for example, into the skin of a finger pad of a patient in order to create a perforation in the skin. The speed of the puncturing movement is preferably controlled so as to ensure puncturing with the least possible pain.

In this context, a sample recovery movement is a movement in which the test element, in particular, a test element on an analysis tape, is moved forward and then back again by a defined distance. This movement is preferably slower than the puncturing movement. In the sample recovery movement, a sample recovery site (e.g., an inlet of a capillary for transporting a sample to the test field of the test element or the test field itself) can emerge by a defined distance from an opening provided for this purpose in a housing of the system according to the invention for collecting samples, such that the sample comes into contact with the sample recovery site and can be transferred onto the latter.

The invention also relates to a method for collecting a liquid sample in a sample-collecting system by means of at least one analytical aid, the analytical aid comprising a lancet and a test element, and the test element having a test field for analysis of the liquid sample. In the method, a coupling element of the system for collecting samples is successively connected to the lancet, in a first position of the analytical aid and to the test element in a second position of the analytical aid. A drive unit moves the coupling element from a rest position to a deployed position, such that the movement of the coupling element is transmitted to the lancet, coupled thereto, in order to execute a puncturing movement, or is transmitted to the test element, coupled thereto, in order to execute a sample recovery movement.

These teachings provide a simple and inexpensive construction of a system for collecting samples. By using the same coupling element to move the lancet (execution of the puncturing stroke) and then the test element (collection of a sample to be analyzed), the structural space taken up by the system according to the invention for collecting samples is kept small.

Moreover, by means of the separate, successive connection of the coupling element to the analytical aid, the coupling mechanism and the drive unit can be considerably simplified in technical terms. A separate drive device for driving the lancet is not required, which likewise considerably reduces the outlay in construction terms.

According to one embodiment, the drive unit comprises a mechanical energy reservoir that can output its energy to the coupling element for moving the latter to the deployed position, and if appropriate, a motor for charging the mechanical energy reservoir. To achieve puncturing with the least possible pain, the lancet should undergo considerable acceleration, such that the lancet penetrates at high speed into the body part in the puncturing movement. It is for this purpose that the mechanical energy reservoir is preferably provided, at least some of whose stored energy can be converted into kinetic energy of the lancet. After the puncturing movement has been carried out, the energy reservoir is substantially or completely uncharged. A motor can then supply the mechanical energy reservoir with energy for the next puncturing movement. However, the charging can also be done manually. An example of a preferred mechanical energy reservoir is a spring which, for charging, is expanded or compressed by the motor or manually by a patient, and which relaxes in order to transfer energy to the lancet. A mechanical energy reservoir is characterized by a high release speed.

The motor that is optionally present for charging the mechanical energy reservoir is preferably an electric motor (in particular a DC motor, brushless external rotor motor) or a shape memory alloy actuator.

The drive unit preferably comprises a mechanical movement converter, and the coupling element is connected to the mechanical energy reservoir via the mechanical movement converter. The mechanical movement converter is a means by which, among other things, the energy released by the energy reservoir is converted mechanically into the desired movement of the coupling element, which leads to the puncturing movement of the lancet. The mechanical movement converter transmits energy of the mechanical energy reservoir to the coupling element, which leads to a movement of the coupling element from its rest position to the deployed position and back again to the rest position, such that the lancet connected to the coupling element executes a puncturing movement. The drive unit of the system according to the invention for collecting samples can be designed, and the mechanical movement converter particularly can be designed, such that, during charging of the mechanical energy reservoir, the drive unit or the mechanical movement converter transmits energy (e.g., of the motor) to the coupling element in order to execute the sample recovery movement by the test element. In particular, a charging movement applied, for example, by the motor or manually by a patient for the purpose of charging the energy reservoir (for example, a tensioning movement for tensioning a spring) can at the same time be transmitted by the mechanical movement converter to the coupling element in order to execute the sample recovery movement by the test element. Thus, only a single motor or a single maneuvering step by the patient is needed for the puncturing movement, or for preparation of the puncturing movement, and for the sample recovery movement, which once again means that the system according to the invention for collecting samples takes up less space.

A possible embodiment of this variant is an electric motor which is provided for tensioning a spring that serves as a mechanical energy reservoir. The energy released by the tensioned spring is transmitted via the mechanical movement converter to the coupling element connected to the lancet. The coupling element is in this way moved from the rest position to the deployed position and back, as a result of which the lancet executes the puncturing movement. The analytical aid is then transported from the first position to the second position, in which the test element is connected to the coupling element. The motor then tensions the spring (charging of the mechanical energy reservoir), and at the same time the tensioning movement driven by the motor is transmitted by the mechanical movement converter to the coupling element connected to the test element. The coupling element is in this way moved from the rest position to the deployed position and back, as a result of which the test element executes the sample recovery movement. The spring is then tensioned again and ready for driving a further puncturing movement. This preferred embodiment of the invention is therefore based on the movement for charging the mechanical energy reservoir (e.g., the tensioning of a spring) being exploited as a useful movement, namely for executing a sample recovery movement by the test element.

The invention further relates to a method for collecting a liquid sample in a sample-collecting system, with the method steps of:
  recovering the liquid sample onto an analytical aid, which comprises a lancet and a test element with a test field for analysis of the liquid sample, by driving a coupling element connected to the test element (e.g., manually or by means of a motor) in order to execute a sample recovery movement by the test element and
  at the same time charging a mechanical energy reservoir (e.g., manually or by the motor) with energy in order to drive a puncturing movement of the lancet connected to the coupling element,
in which method the coupling element is connected successively to the lancet and to the test element and is moved from a rest position to a deployed position and back to the rest position, both in the puncturing movement and also in the sample recovery movement.

According to one exemplary embodiment, the mechanical movement converter has a slide with a guide slot into which an engagement element arranged on the coupling element engages. The mechanical energy reservoir and, if appropriate, a motor are preferably connected to the slide body via a drive element, such that energy of the mechanical energy reservoir is transmitted to the slide body in order to move the slide body in a first direction relative to the coupling element, and, during charging of the mechanical energy reservoir, energy (e.g., of the motor) can be transmitted to the slide body in order to move the slide body relative to the coupling element in a second direction counter to the first direction. The slide body can consequently be moved by the energy reservoir in one direction and, for example, manually or by the motor in the other direction. By contrast, the coupling element is fixed in position along the direction of movement of the slide body, but it can be moved perpendicularly with respect to the direction of movement from the rest position to the deployed position. During the movement of the slide body, the engagement element of the coupling element is guided along the guide slot which, as a curved guide, causes the coupling element to be deployed perpendicularly with respect to the movement of the slide body. The guide slot is designed symmetrically with a highest point arranged between two lowest points, such that the coupling element undergoes a movement stroke from the rest position to the maximally deployed position and back to the rest position both in the forward movement and also in the return movement of the slide body. The forward movement of the slide body is driven by a spring, for example, and the return movement is driven by an electric motor, for example, upon renewed tensioning of the spring. After the forward movement has been executed and before the return movement, the lancet is disconnected from the coupling element, and the test element, in particular, a test element on an analysis tape, is connected to the coupling element.

According to another embodiment, the mechanical movement converter is constructed as a connecting rod drive, which connecting rod drive has a connecting rod and a drive rotor which interact with the coupling element in such a way that a rotating movement of the drive rotor can be converted into a linear movement of the coupling element.

The drive rotor (e.g., a drive shaft) can therefore be rotated in one direction by the mechanical energy reservoir (e.g., a coil spring) and in the other direction (e.g., by a motor). Upon rotation of the drive rotor, the movement of rotation is converted by the connecting rod into a linear movement of the coupling element. The angle of rotation is chosen such that the coupling element undergoes a movement stroke from the rest position to the maximally deployed position and back again, both in the forward movement and also in the return movement of the drive rotor. The forward rotation is driven by a coil spring, for example, and can be quick. The return rotation can be driven by an electric motor or manually, for example, upon renewed tensioning of the coil spring.

The terms "quick" and slow can be illustrated, for example, on the basis of the puncture time in the "quick" lancet movement. For example, the speed of the lancet movement can be such that a puncture time of ca. 2-3 ms is needed for the last millimeter of the stroke. For a total stroke of 2 mm in 2-3 ms, this means a speed of ca. 0.66 m/s. Generally, the speeds can preferably lie between ca. 0.2 m/s and ca. 5 m/s, with preference being given to speeds between 0.5 and 1 m/s. For the "slow" sample recovery movement, a total stroke of ca. 17 mm can take place in a time of 1-2 seconds for example, which results in a speed of ca. 0.85 mm/s to ca. 1.7 mm/s. Generally, speeds in the range of ca. 0.5 mm/s to ca. 5 mm/s are preferred. In this movement, the dwell time at the amplitude peak can be, for example, in the range of 0.5 s, preferably in the range between 0.2 and 2 s.

After the forward rotation has been executed, and before the return rotation, the lancet is disconnected from the coupling element, and the test element is connected to the coupling element (or at least made ready for connection).

The drive unit of the system according to the invention for collecting samples preferably comprises a drive element that performs at least the following three functions:

1. transferring energy from the energy reservoir as kinetic energy to the coupling element, and thus to the lancet connectable thereto, in order to execute a puncturing movement;
2. transferring energy from the motor, or energy input manually by a user, as kinetic energy to the coupling element, and thus to the test element connectable thereto, in particular a test element on an analysis tape, in order to execute a sample recovery movement; and
3. transferring energy from the motor, or energy input manually by a user, to the mechanical energy reservoir for the purpose of charging the mechanical energy reservoir.

In the embodiment variant with the slide, such a drive element can, for example, be in the form of a carrier element which is moved in one direction upon expansion of a spring (mechanical energy reservoir) and is moved in the other direction manually by a user or by the motor, and which tensions the spring in the movement driven manually by a user or by the motor and carries the slide body along in both movements (by the spring and the user/motor).

In the embodiment variant with a connecting rod drive, such a drive element can be in the form of a drive rotor which is rotated in one direction of rotation upon relaxation of a spring (mechanical energy reservoir) and is rotated in the other direction of rotation manually by a user or by the motor, and which tensions the spring in the rotation driven manually by a user or by the motor and carries the connecting rod and therefore the coupling element along in both rotations (by the spring and the motor).

The invention further relates to a system for collecting samples, designed for collecting a liquid sample and comprising a lancet, a housing and a drive unit for driving the lancet such that the lancet can emerge at least partially from the housing in order to execute a puncturing movement. The drive unit comprises a mechanical energy reservoir which can output its energy to the lancet in order to execute a puncturing movement, and, if appropriate, a motor for charging the mechanical energy reservoir. The drive unit comprises a mechanical movement converter, the lancet being connected to the mechanical energy reservoir via the mechanical movement converter, and the mechanical movement converter comprises a connecting rod drive. The connecting rod drive comprises a connecting rod and a drive rotor that interact with the lancet in such a way that a rotating movement of the drive rotor can be converted into a linear movement of the lancet.

In addition, the mechanical movement converter or the motor can be connected to a further system function which is independent of the mechanical energy reservoir and which is part of the system for collecting samples, or of an analysis system comprising the system for collecting samples. The system function independent of the mechanical energy reservoir can, for example, be at least one of the functions from the following group: execution of the sample recovery movement of the test element, transporting of an analytical aid comprising the lancet, transporting of a test element, and transporting of a test element magazine. According to this embodiment, for example, the motor is used as a combined drive. In the combined drive, the (preferably electrically operated) motor charges the mechanical energy reservoir and actuates a further system function at the same time as or at a different time from the charging of the mechanical energy reservoir. In the above-described system for collecting samples, this is the system function concerning execution of the sample recovery movement by the test element.

Therefore, a system for collecting samples is possible with a combination drive, in which a drive mechanism (e.g., a motor, in particular an electric motor) is connected to several system functions. One of these system functions preferably concerns transporting an analysis tape with at least one analytical aid. This transport of the tape is preferably such that the analysis tape is transported relative to a housing of the sample-collecting system and/or relative to a housing of a tape cassette of the sample-collecting system. In addition, the combination drive is used for connection to at least one further system function. These at least two system functions of the system for collecting samples can, for example, be once again chosen from the abovementioned group of system functions. Moreover, this concept of the combination drive can also be implemented independently of the aforementioned preferred features of the proposed system for collecting samples, although it is preferably combined with the preferred embodiments of the above-described systems for collecting samples.

The invention further relates to a system for collecting samples, designed for collecting a liquid sample and comprising at least one analytical aid, with a lancet and a test element, and comprising a mechanical energy reservoir (e.g., a spring) which can output energy to the lancet in order to execute a puncturing movement. The system for collecting samples comprises transmission means that are connected to the mechanical energy reservoir and to the analytical aid such that a movement of the transmission means simultaneously transmits energy to the mechanical energy reservoir, in order to charge the mechanical energy reservoir, and moves the test element. This system for collecting samples can include a large number of features from the above-described systems for collecting samples.

The invention also relates to a method for collecting a liquid sample in a sample-collecting system by means of at least one analytical aid, and to a system for carrying out the method according to the invention, the analytical aid comprising a lancet and a test element. A movement by transmission means of the system for collecting samples, which movement serves to charge a mechanical energy reservoir with energy in order to drive a puncturing movement of the lancet, is at the same time used to move the test element.

The transmission means according to the present invention can be means that transmit energy to the mechanical energy reservoir in order to charge the mechanical energy reservoir. For example, these are means that are used to tension a spring provided as a mechanical energy reservoir. The charged mechanical energy reservoir can then output energy in order to drive a puncturing movement of the lancet of the analytical aid. If the mechanical energy reservoir is a spring, for example, its relaxation can be used to output energy to the lancet in order to execute the puncturing movement.

In order to charge the mechanical energy reservoir, at least one component part of the transmission means is moved. The component part executes a linear translation movement or a rotation movement, for example. By means of this movement, energy is transmitted to the mechanical energy reservoir (a spring is tensioned, for example). The movement of the component part of the transmission means leads additionally, and preferably independently of the charging of the mechanical energy reservoir, to a movement of the test element, for example, to a sample recovery movement by which a liquid sample is taken up onto a test field of the test element. For example, the movement of the component part of the transmission means results in a movement of a further component part of the transmission means, which drives the movement of the test element.

The invention also relates to a method for collecting a liquid sample in a sample-collecting system by means of at least one analytical aid, and to a system for carrying out the method, the analytical aid comprising a lancet and a test element. A movement by transmission means of the system for collecting samples, which movement serves to charge a mechanical energy reservoir with energy in order to drive a puncturing movement of the lancet, is at the same time used to move the test element. The transmission means can, for example, comprise a connecting rod drive or a slide body with a guide slot.

In the case of a connecting rod drive, for example, a rotation movement of the drive rotor can serve to tension a spring (charging of the mechanical energy reservoir). The drive rotor can be rotated by a motor or manually by a user, for example. The connecting rod mounted on the drive rotor is moved by the rotation movement of the drive rotor. This movement of the connecting rod in turn drives a movement (e.g., a sample recovery movement) of the test element (independently of the tensioning of the spring).

In the case of a slide, for example, a translation movement of the slide body is used to tension a spring (charging of the mechanical energy reservoir). For this purpose, the slide body can by moved by a motor or manually by a user, for example. As a result of the translation movement of the slide body, the guide slot present in the latter is also moved, as also is an engagement element engaging in the guide slot. This movement of the engagement element (guided by the guide slot) in turn drives a movement (e.g., a sample recovery movement) of the test element (independently of the tensioning of the spring).

Moreover, the transmission means, in a first movement, can transmit energy of the mechanical energy reservoir to the lancet in order to execute the puncturing movement and, in a second movement, can simultaneously transmit energy for charging the mechanical energy reservoir and drive the test element.

In the case of a connecting rod drive, for example, a rotation movement of the drive rotor in one direction can serve to tension a spring (charging of the mechanical energy reservoir), and a rotation movement of the drive rotor in the other direction (relaxation of the spring, discharging of the mechanical energy reservoir) can be transmitted via the connecting rod to the lancet, in order to execute the puncturing movement.

In the case of a slide, for example, a translation movement of the slide body in one direction is used to tension a spring (charging of the mechanical energy reservoir), and a translation movement of the slide body in the other direction (relaxation of the spring, discharging of the mechanical energy reservoir) is transmitted via the guide slot and the engagement element to the lancet, in order to execute the puncturing movement.

The invention further relates to an analysis system for analyzing a liquid sample, which analysis system comprises a system according to the invention for collecting samples and a measurement arrangement.

The analysis system can be designed to carry out electrochemical and/or photometric analysis.

In the case of photometric analysis systems, the test elements may contain a reagent system, the reaction of which with the analyte leads to a photometrically detectable change (a change in color). The reagents are in this case usually located in a test field of the test element, the color of which changes in dependence on the concentration. This change in color can be determined quantitatively by reflection photometry with the aid of a measurement arrangement.

Electrochemical test elements contain an electrochemical reagent system, the reaction of which with the analyte influences the electric voltage between two poles of the test element and/or of the current intensity flowing between two poles of a test element with a defined voltage. In this case, the voltage or current intensity is therefore the physically measurable variable that is determined by a corresponding measurement arrangement, which is integrated in the analysis system and designed as a voltage or current measurement device, and a change of which that correlates with the concentration of the analyte is converted into the analysis data (concentration of the analyte).

The invention further relates to the use of a system according to the invention for collecting a blood sample and to the use of an analysis system according to the invention for analyzing the glucose content in a body fluid.

Further details and features of the invention will become clear from the following description of illustrative embodiments. The respective features can be embodied either singly or in several combinations with one another, though the invention is not limited to the illustrative embodiments.

BRIEF DESCRIPTION OF THE DRAWINGS

The above-mentioned aspects of the present invention and the manner of obtaining them will become more apparent and the invention itself will be better understood by reference to the following description of the embodiments of the invention, taken in conjunction with the accompanying drawings, wherein.

Corresponding reference characters indicate corresponding parts throughout the several views.

DETAILED DESCRIPTION

The embodiments of the present invention described below are not intended to be exhaustive or to limit the invention to the precise forms disclosed in the following detailed description. Rather, the embodiments are chosen and described so that others skilled in the art may appreciate and understand the principles and practices of the present invention.

Figure 1A:
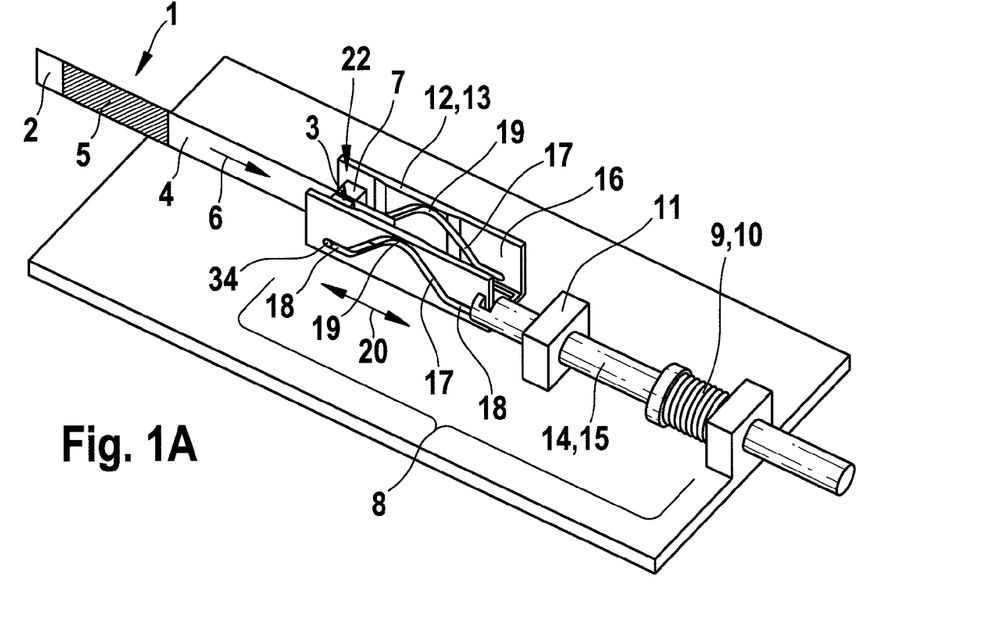
FIGS. 1A to 1F show the sequence of movement in a schematically illustrated first embodiment of a system according to the invention for collecting samples, with a slide.

FIG. 1A is a schematic representation of a first embodiment of a system for collecting samples, in the initial state. The system for collecting samples comprises an analytical aid 1, which is an analytical aid 1 arranged on an analysis tape 2. Only a portion of the analysis tape 2 is shown. The analytical aid 1 comprises a lancet 3 and a test element 4. The test element 4 has a test field 5 for analysis of a liquid sample, in particular, for analysis of a sample of blood. The analysis tape 2 can be conveyed in the direction of transport 6 by means of a transport device (not shown). The lancet 3 is arranged perpendicular to the direction of transport 6 on the analytical aid 1.

The system for collecting samples comprises a coupling element 7 in the form of a gripper which, in FIG. 1A, is connected to the lancet (first position of the analytical aid 1). The system for collecting samples further comprises a drive unit 8 for moving the coupling element 7. The drive unit 8 comprises a spring 9 as mechanical energy reservoir 10, a motor 11, a slide 12 as mechanical movement converter 13, and a carrier 14 which, as drive element 15, connects the mechanical energy reservoir 10, the motor 11 and the slide body 16 of the slide 12 to one another. The spring 9 is tensioned (charged mechanical energy reservoir 10). The slide 12 comprises the slide body 16, which has a guide slot 17. The guide slot 17 has a highest point 19 arranged between two lowest points 18 and is designed symmetrically. An engagement element 34 of the coupling element 7 engages in the guide slot 17. The coupling element 7 is fixed in position relative to the possible direction of movement 20 of the slide body 16. It can only be moved perpendicular to this direction of movement 20 by the guide slot 17, in which its engagement element 34 engages. In FIG. 1A, the coupling element 7 is shown in its rest position 22.

Figure 1B:
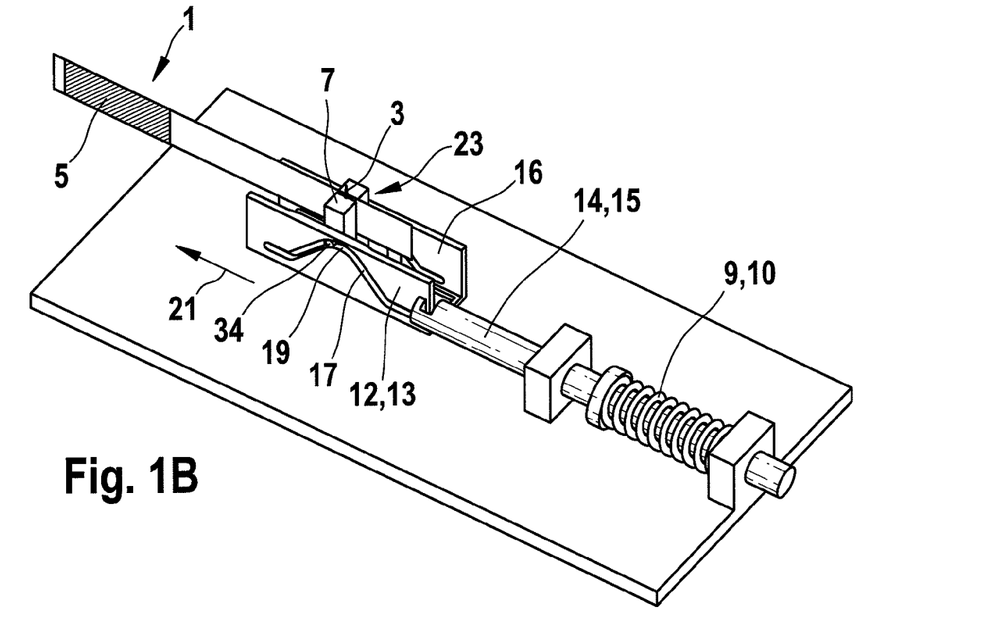

FIG. 1B shows the sample-collecting system from FIG. 1A after the puncturing procedure has been initiated. The initiation has the result that the tensioned spring 9 relaxes, and the mechanical energy reservoir 10 outputs at least some of its stored energy as kinetic energy to the slide body 16 via the drive element 15. The slide body 16 is thereby moved in a first direction 21 relative to the coupling element 7. The engagement element 34 of the coupling element 7 thus runs along the guide slot 17, as a result of which the coupling element 7 is lifted from the rest position to the deployed position 23 shown in FIG. 1B. The coupling element 7 has reached the highest point 19 of the guide slot 17. The lancet 3, connected to the coupling element 7, is thus also lifted and, as a result of this movement, pierces, for example, into a part of the body of a patient, in order to create an opening in the skin and collect a sample of blood.

Figure 1C:
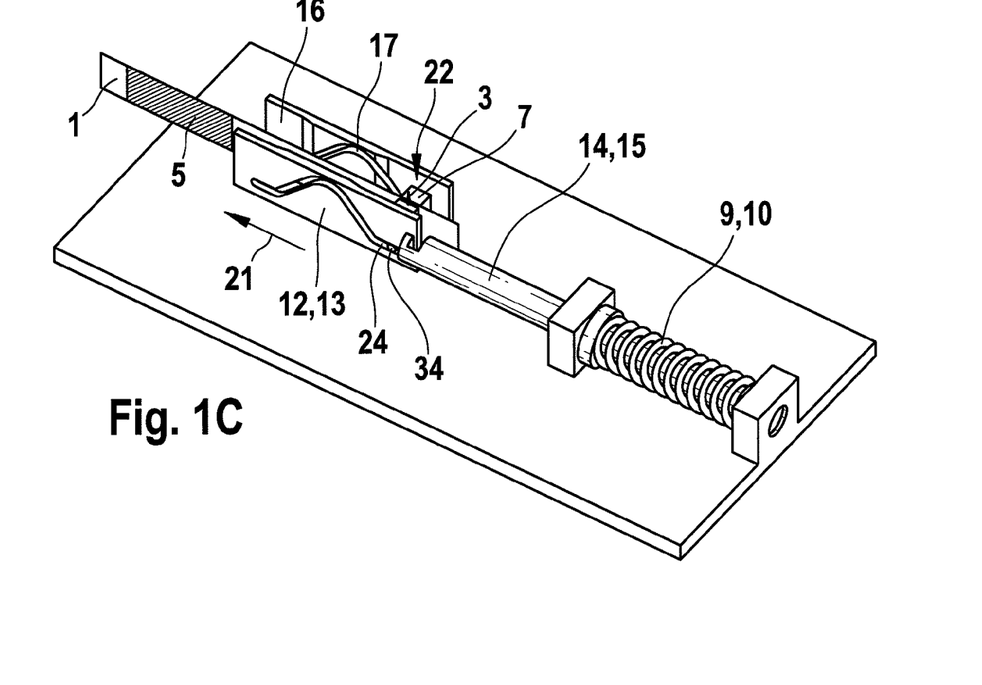

FIG. 1C shows the sample-collecting system from FIGS. 1A and 1B after a puncturing movement has been carried out. After the coupling element 7 has reached the highest point 19 of the guide slot 17, the continued relaxation of the spring 9 means that the slide body 16 moves still further in the first direction 21 relative to the coupling element 7. The engagement element 34 of the coupling element 7 moves farther along the guide slot 17 until the spring 9 is fully relaxed. In this state, the coupling element 7 is located at the second lowest point 24 of the guide slot 17, such that it is again in its rest position 22. The lancet 3 is now retracted again and has thus completed its puncturing movement.

Figure 1D:
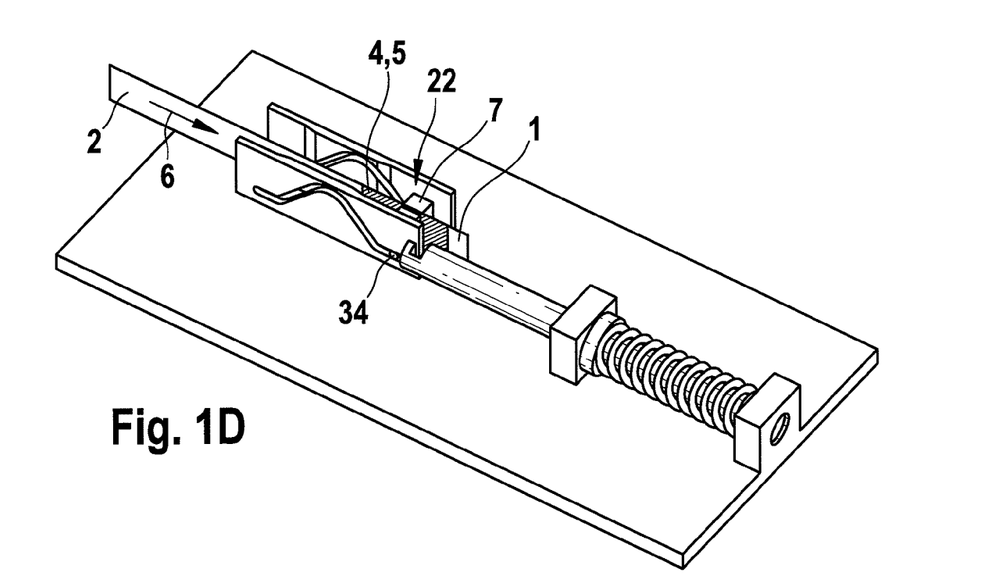

FIG. 1D shows the sample-collecting system from FIGS. 1A to 1C after the analytical aid has been transported onward. After the lancet 3 has carried out the puncturing movement, a transport device (not shown) transports the analytical aid 1 in the direction of transport 6, relative to the coupling element 7 arranged in the rest position 22, from the first position to the second position in which the coupling element 7 is connected to the test element 4. For this purpose, the analysis tape 2, which carries the analytical aid 1, is reeled forward in the direction of transport 6 until the desired second position for connecting the test element 4 to the coupling element 7 is reached.

Figure 1E:
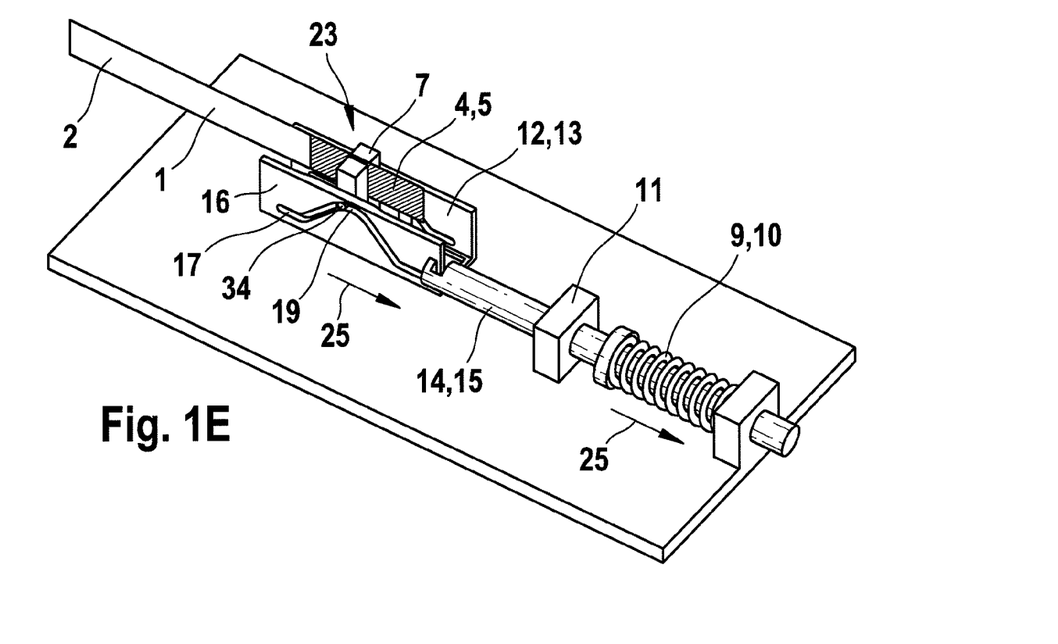

FIG. 1E shows the sample-collecting system from FIGS. 1A to 1D during the sample recovery movement by the test element. The test element 4 is connected to the coupling element 7. The motor 11 moves the drive element 15 in the second direction 25, counter to the first direction 21. In this way, the slide body 16 connected to the drive element 15 is moved in the second direction 25 relative to the coupling element 7. The engagement element 34 of the coupling element 7 runs along the guide slot 17 in the opposite direction to that in FIG. 1B, as a result of which the coupling element 7 is lifted from the rest position to the deployed position 23 shown in FIG. 1E. The coupling element 7 has reached the highest point 19 of the guide slot 17. The movement of the coupling element 7 is transmitted to the test element 4 coupled thereto, such that the test element 4 is likewise lifted and, by means of this sample recovery movement, is brought into contact with, for example, a sample of blood on a part of the body of a patient.

At the same time, the spring 9 is tensioned (charging of the mechanical energy reservoir 10) by the motor 11 via the movement of the drive element 15 in the second direction 25. The energy of the motor 11 is therefore used simultaneously to charge the mechanical energy reservoir 10 and to move the slide body 16 in the second direction 25 relative to the coupling element 7. The slide 12 and the drive element 15 are designed such that, during charging of the mechanical energy reservoir 10, they transmit energy of the motor 11 to the coupling element 7, in order to execute the sample recovery movement by the test element 4. This is achieved in particular by the way in which the slide 12, motor 11 and mechanical energy reservoir 10 are connected to the drive element 15.

Figure 1F:
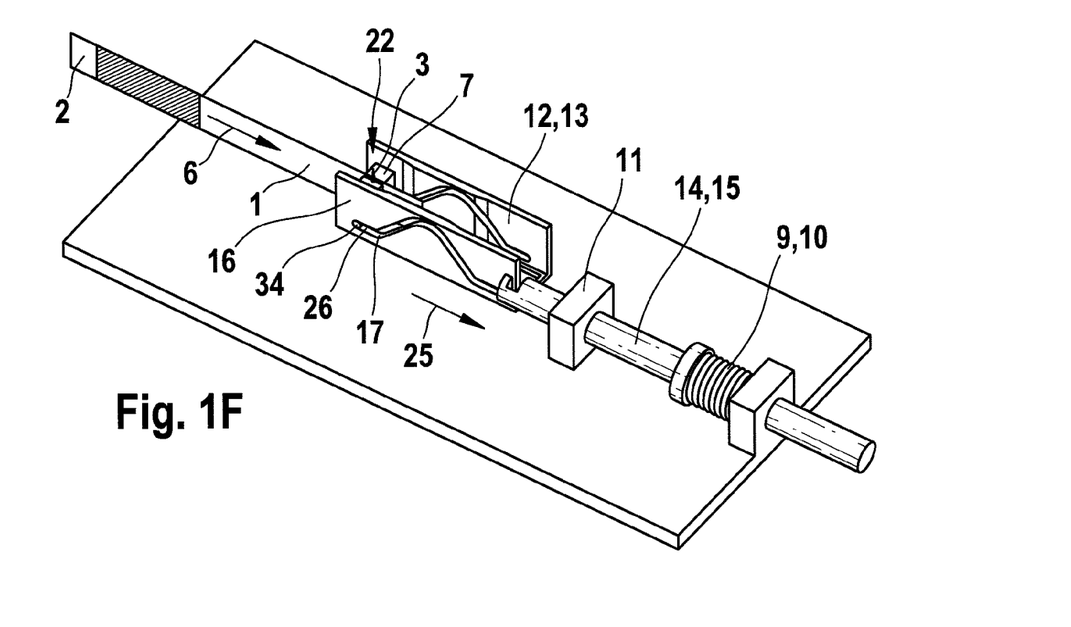

FIG. 1F shows the sample-collecting system from FIGS. 1A to 1E after a sample recovery movement has been carried out. After the coupling element 7 has reached the highest point 19 of the guide slot 17, the slide body 16 is moved further by the motor 11 and drive element 15 in the second direction 25 relative to the coupling element 7, with the spring at the same time being tensioned again by the drive element. The engagement element 34 of the coupling element 7 again slides along the guide slot 17 until the spring 9 is fully tensioned and the motor 11 is stopped. In this state, the coupling element 7 is located at the first lowest point 26 of the guide slot 17, such that it is once again in its rest position 22. The test element 4 is now retracted again and has thus completed the sample recovery procedure. The analysis tape 2 is then conveyed by the transport device (not shown) in the direction of transport 6 relative to the coupling element 7, until the first position of the next analytical aid 1 arranged on the analysis tape 2 is again reached. In this first position, as shown in FIG. 1F, the lancet 3 is connected to the coupling element 7. The spring 9 is fully tensioned and ready to output its energy for carrying out a further puncturing movement.

Figure 2A:
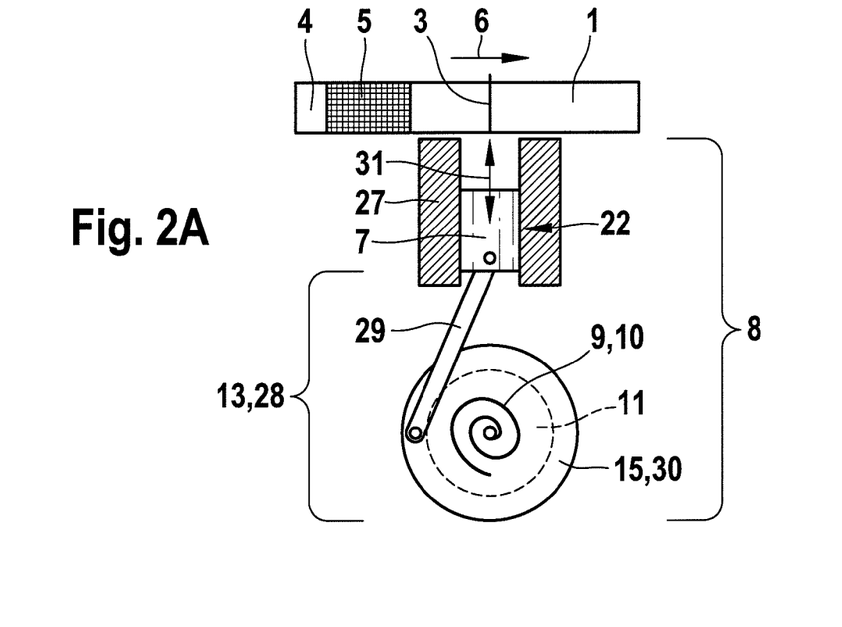
FIGS. 2A to 2F show the sequence of movement in a schematically illustrated second embodiment of a system according to the invention for collecting samples, with a connecting rod drive.

FIG. 2A shows a schematic representation of a second embodiment of a system for collecting samples, in the initial state. The system for collecting samples comprises an analytical aid, which can be an analytical aid 1 on its own, or one arranged on an analysis tape. The analytical aid 1 comprises a lancet 3 and a test element 4. The test element 4 has a test field 5 for analysis of a liquid sample, in particular, for analysis of a sample of blood. The analytical aid 1 can be conveyed in the direction of transport 6 by means of a transport device (not shown). The lancet 3 is arranged perpendicular to the direction of transport 6 on the analytical aid 1.

The system for collecting samples comprises a coupling element 7 in the form of a ram, which is guided via a guide means 27 in the direction of the analytical aid, said coupling element 7 in FIG. 2A being connectable to the lancet 3 (first position of the analytical aid 1). The system for collecting samples further comprises a drive unit 8 for moving the coupling element 7. The drive unit 8 comprises a spring 9 as mechanical energy reservoir 10, a motor 11 and a connecting rod drive 28 as mechanical movement converter 13. The spring 9 is tensioned (charged mechanical energy reservoir 10). The connecting rod drive 28 comprises a connecting rod 29 and a drive rotor 30, which interact with the coupling element 7 such that a rotating movement of the drive rotor 30 is converted via the connecting rod 29 into a linear movement 31 (guided by the guide means 27) of the coupling element 7. The motor 11 is connected to the drive rotor 30, such that it can rotate the latter about a defined angle of rotation when necessary (in particular for tensioning the spring 9). The spring 9 is connected to the drive rotor 30, such that it rotates the drive rotor 30 about a defined angle of rotation when converted from the tensioned to the relaxed state. The spring 9 outputs the stored energy as kinetic energy to the drive rotor 30. The drive rotor 30 is connected to the coupling element 7 via the connecting rod 29. The drive rotor 30 is therefore a drive element 15 which connects the motor 11, the mechanical energy reservoir 10 (spring 9) and the coupling element 7 to one another. In FIG. 2A, the coupling element 7 is shown in its rest position 22.

Figure 2B:
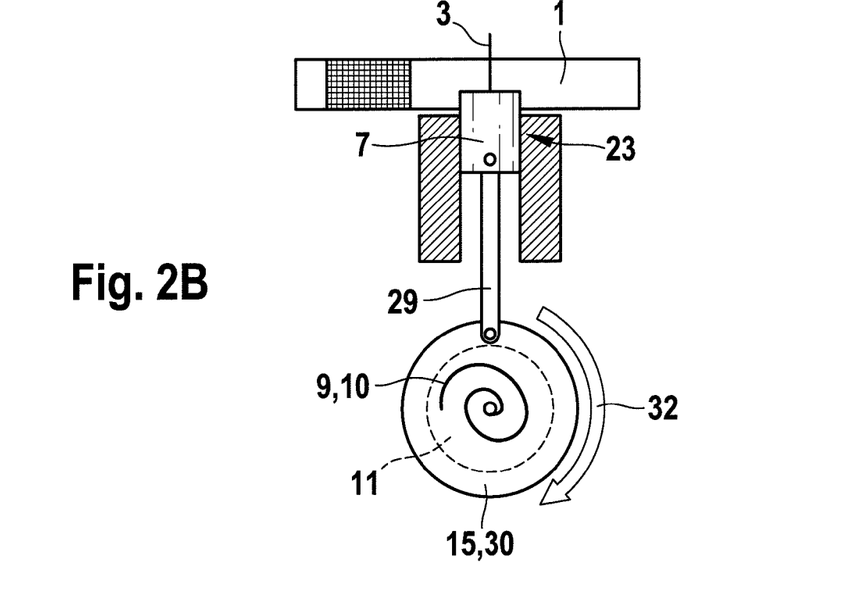

FIG. 2B shows the sample-collecting system from FIG. 2A after the puncturing procedure has been initiated. The initiation has the result that the tensioned spring 9 relaxes, and the mechanical energy reservoir 10 outputs at least some of its stored energy as kinetic energy to the connecting rod 29 via the drive rotor 30. The energy of the spring 9 is transmitted for this purpose to the drive rotor 30 in order to rotate the drive rotor 30 in a first direction of rotation 32, as a result of which the connecting rod 29 is moved in the direction of the analytical aid 1. In this way, the coupling element 7 (guided by the guide means 27) is lifted from the rest position to the deployed position 23 shown in FIG. 2B. The lancet 3, connected to the coupling element 7, is thus also lifted and, as a result of this movement, pierces, for example, into a part of the body of a patient, in order to create an opening in the skin and collect a sample of blood. The lifting movement of the lancet 3 is shown only schematically in FIG. 2B, and the analytical aid 1 is in practice moved at least partially with the lancet 3.

Figure 2C:
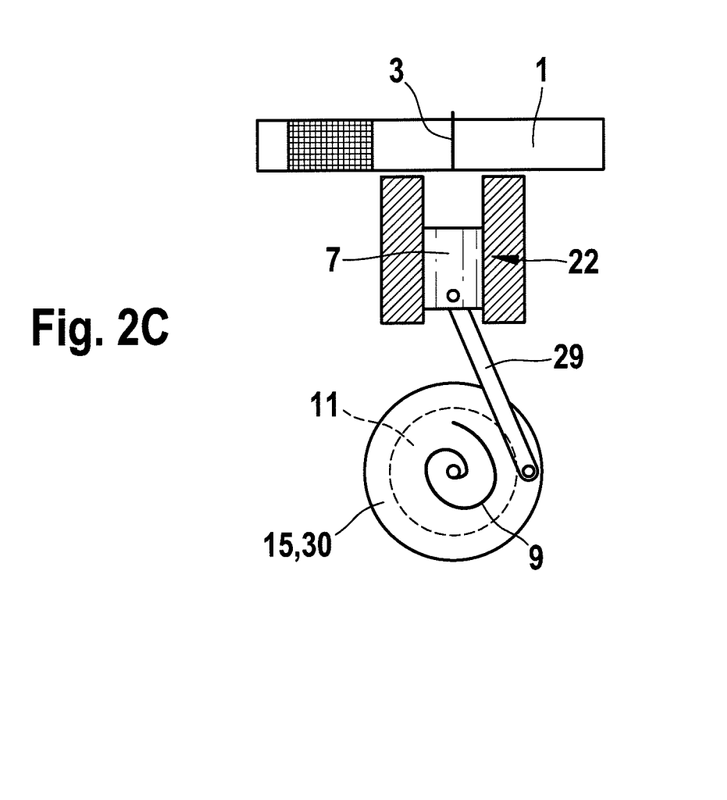

FIG. 2C shows the sample-collecting system from FIGS. 2A and 2B after a puncturing movement has been carried out. After the coupling element 7 has reached the maximum excursion (as is shown in FIG. 2B), the continued relaxation of the spring 9 means that the drive rotor 30 rotates still further in the first direction of rotation 32, until the spring 9 is more or less fully relaxed. In this state, the connecting rod 29 is drawn back again from the analytical aid, such that the coupling element has likewise been moved back to its rest position 22. In this way, the lancet 3 is retracted again and has thus completed its puncturing movement.

Figure 2D:
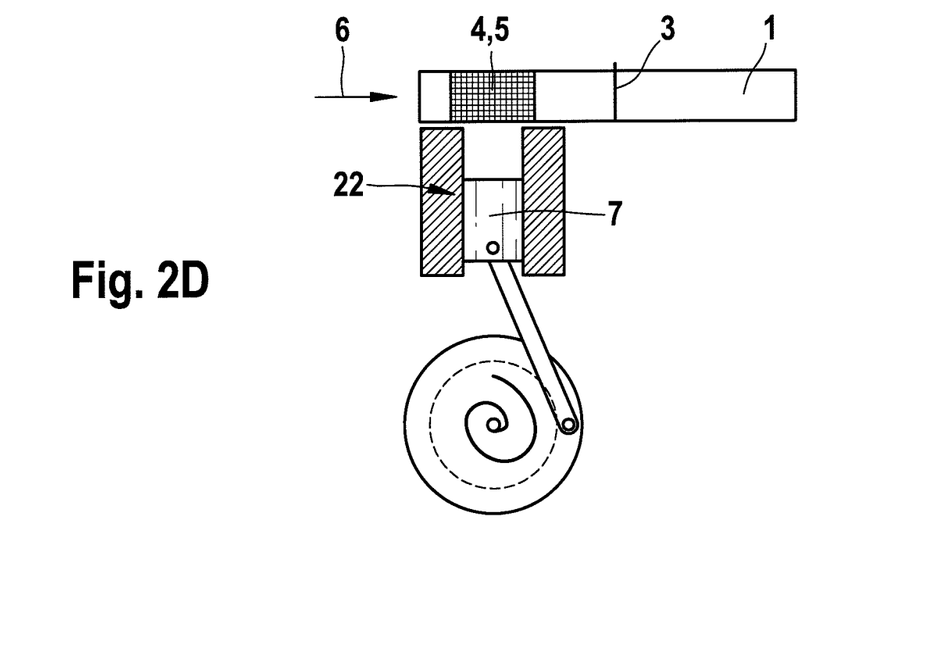

FIG. 2D shows the sample-collecting system from FIGS. 2A to 2C after the analytical aid has been transported onward. After the lancet 3 has carried out the puncturing movement, a transport device (not shown) transports the analytical aid 1 in the direction of transport 6, relative to the coupling element 7 arranged in the rest position 22, from the first position to the second position, in which the coupling element 7 can be connected to the test element 4.

Figure 2E:
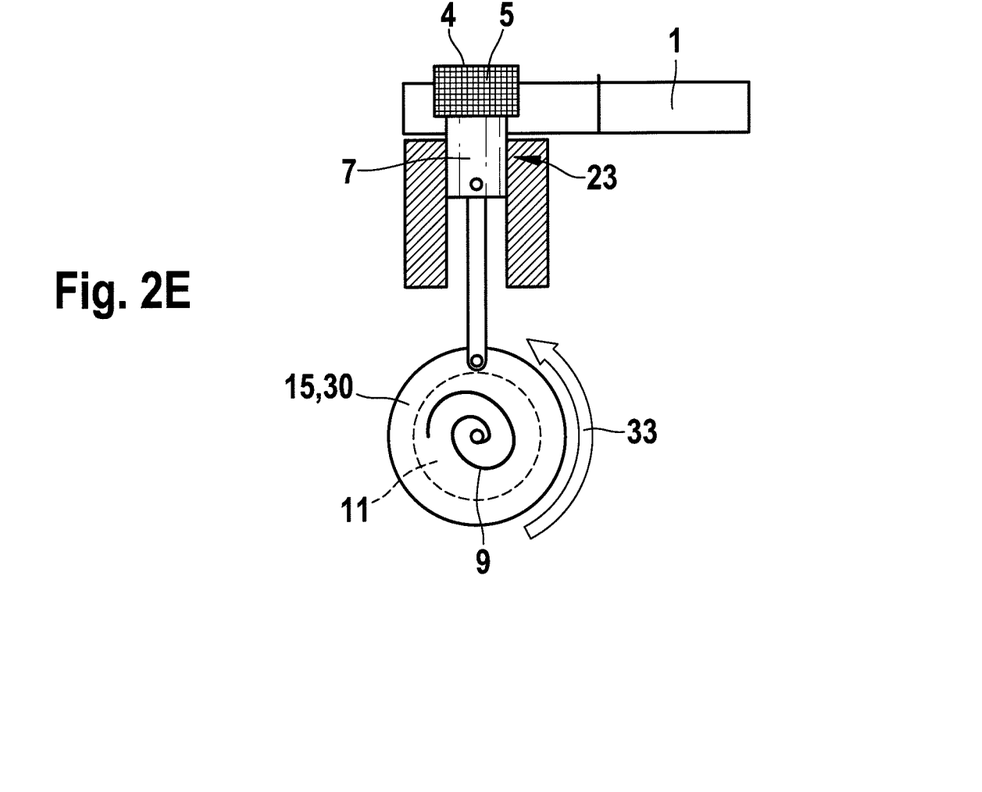

FIG. 2E shows the sample-collecting system from FIGS. 2A to 2D during the sample recovery movement by the test element. The test element 4 is connected to the coupling element 7. The motor 11 moves the drive rotor 30 (drive element 15) in the second direction of rotation 33, counter to the first direction of rotation 32. In this way, the connecting rod 29 coupled to the drive rotor 30 is moved again in the direction of the analytical aid, as a result of which the coupling element 7 (guided by the guide means 27) is lifted from the rest position to the deployed position 23 shown in FIG. 2E. The movement of the coupling element 7 is transmitted to the test element 4 connected thereto, such that the test element 4 is likewise lifted and, by means of this sample recovery movement, is brought into contact with, for example, a sample of blood on a part of the body of a patient. The lifting movement of the test element 4 is shown only schematically in FIG. 2E by the lifting of the test field 5, and the analytical aid 1 is in practice moved at least partially, preferably completely, with the test element 4.

At the same time, the spring 9 (not shown) is tensioned (charging of the mechanical energy reservoir 10) by the motor 11 via the rotation of the drive rotor 30 (drive element 15) in the second direction of rotation 33. The energy of the motor 11 is therefore used simultaneously to charge the mechanical energy reservoir 10 and to move the connecting rod 29. The drive rotor 30 and the connecting rod 29 are designed such that, during charging of the mechanical energy reservoir 10, they transmit energy of the motor 11 to the coupling element 7, in order to execute the sample recovery movement by the test element 4. This is achieved in particular by the way in which the connecting rod 29, motor 11 and mechanical energy reservoir 10 are connected to the drive rotor 30 (drive element 15).

Figure 2F:
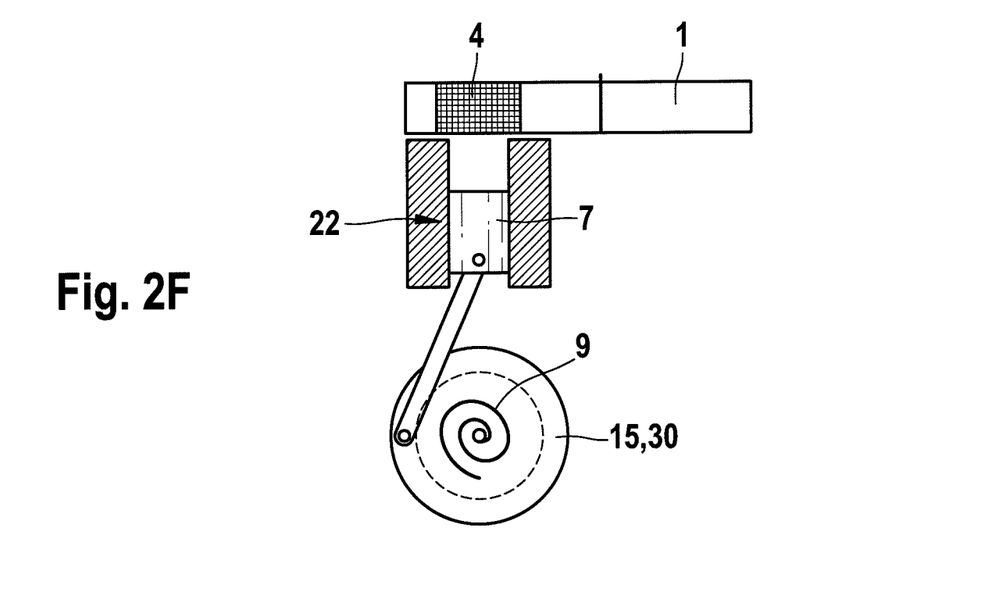

FIG. 2F shows the sample-collecting system from FIGS. 2A to 2E after a sample recovery movement has been carried out. After the coupling element 7 has reached the maximum excursion (as is shown in FIG. 2E), the drive rotor 30 is moved further by the motor 11 in the second direction of rotation 33. The connecting rod 29 is drawn back again in this way, until the spring 9 is fully tensioned and the motor 11 is stopped. In this state, the coupling element 7 is once again in its rest position 22. The test element 4 is now retracted again and has thus completed the sample recovery procedure. The sequence of movement from FIGS. 2A to 2F can now be repeated with a new analytical aid 1.

While exemplary embodiments incorporating the principles of the present invention have been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

LIST OF REFERENCE NUMBERS 1 analytical aid
2 analysis tape
3 lancet
4 test element
5 test field
6 direction of transport
7 coupling element
8 drive unit
9 spring
10 mechanical energy reservoir
11 motor
12 slide
13 mechanical movement converter
14 carrier
15 drive element
16 slide body
17 guide slot
18 lowest points
19 highest point
20 direction of movement of the slide body 21 first direction
22 rest position
23 deployed position
24 second lowest point
25 second direction
26 first lowest point
27 guide means
28 connecting rod drive
29 connecting rod
30 drive rotor
31 linear movement
32 first direction of rotation
33 second direction of rotation
34 engagement element

What is claimed is:

1. A system for collecting liquid samples, comprising:
a housing;
several analytical aids, each analytical aid comprising a lancet and a test element having a test field for analysis of a liquid sample wherein the lancet and the test element are disposed on a support;
a coupling element wherein the support of each analytical aid is positionable in first and second positions relative to the coupling element to thereby respectively define first and second positions of the analytical aid; and
a drive unit configured to move the coupling element from a rest position to a deployed position, a selected one of the analytical aids being moveable relative to the coupling element from the first position to the second position when the coupling element is in the rest position and wherein during the movement of the coupling element from the rest position to the deployed position when the one analytical aid is positioned in the first position, the coupling element is connectable to the lancet of the one analytical aid to execute a puncturing movement, and during the movement of the coupling element from the rest position to the deployed position when the one analytical aid is positioned in the second position, the coupling element is connectable to the test element of the one analytical aid to execute a sample recovery movement.

2. The system of claim 1, further comprising a transport device for transporting the support of the analytical aid from the first position to the second position relative to the coupling element arranged in the rest position.

3. The system of claim 1, wherein the drive unit comprises a mechanical energy reservoir that can output energy to and move the coupling element to the deployed position.

4. The system of claim 3, wherein the mechanical energy reservoir comprises a spring.

5. The system of claim 3, wherein the drive unit comprises a motor for charging the mechanical energy reservoir.

6. The system of claim 3, wherein, during charging of the mechanical energy reservoir, the drive unit transmits energy to the coupling element to execute the sample recovery movement of the test element.

7. The system of claim 3, wherein the drive unit comprises a mechanical movement converter and the coupling element is connected to the mechanical energy reservoir via the mechanical movement converter.

8. The system of claim 7, wherein the mechanical movement converter is configured to transmit energy of the mechanical energy reservoir to the coupling element to execute the puncturing movement of the lancet.

9. The system of claim 7, wherein the mechanical movement converter comprises a slide body having a guide slot into which an engagement element arranged on the coupling element engages.

10. The system of claim 9, wherein the mechanical energy reservoir and a motor are connected to the slide body via a drive element, wherein energy of the mechanical energy reservoir is transmitted to and moves the slide body in a first direction relative to the coupling element, and, during the charging of the mechanical energy reservoir, energy of the motor is transmitted to and moves the slide body relative to the coupling element in a second direction counter to the first direction.

11. The system of claim 7, wherein the mechanical movement converter comprises a connecting rod and a drive rotor which interact with the coupling element, wherein a rotating movement of the drive rotor is converted into a linear movement of the coupling element.

12. The system of claim 11, wherein the mechanical energy reservoir and a motor are connected to the drive rotor, wherein energy of the mechanical energy reservoir is transmitted to and rotates the drive rotor in a first direction, and, during charging of the mechanical energy reservoir, energy of the motor is transmitted to and rotates the drive rotor in a second direction counter to the first direction.

13. The system of claim 1, wherein the several analytical aids are received on an analysis tape, on a multiplicity of analytical aids, on a transport tape, in a magazine, or on a test element disk.

14. A system for collecting liquid samples, comprising:
a housing;
an analytical aid having a lancet and a test element disposed on a support;
a mechanical energy reservoir which outputs energy to the lancet to execute a puncturing movement; and
a transmission connected to the mechanical energy reservoir and to a coupling member, the coupling member and the support of the analytical aid being movable relative to each other wherein the coupling member is selectively couplable with the lancet and the test element wherein the mechanical energy reservoir outputs energy through the transmission to drive the lancet when the coupling member is coupled with the lancet and, wherein movement of the transmission simultaneously transmits energy to the mechanical energy reservoir to charge the mechanical energy reservoir and drives a sample recovery movement of the test element when the coupling member is coupled with the test element.

15. The system of claim 14, wherein the transmission in a first movement transmits energy of the mechanical energy reservoir to the lancet to execute the puncturing movement, and in a second movement simultaneously transmits energy to charge the mechanical energy reservoir and moves the test element.

16. The system of claim 15, wherein the first movement is faster than the second movement.

17. The system of claim 14, wherein the transmission comprises a connecting rod drive or a slide body with a guide slot.

18. A system for collecting liquid samples, comprising:
a housing;
a lancet;
a drive unit for driving the lancet such that the lancet can emerge at least partially from the housing in order to execute a puncturing movement, the drive unit comprising:
a mechanical energy reservoir which outputs energy to execute a puncturing movement with the lancet;

a mechanical movement converter, the lancet being connected to the mechanical energy reservoir via the mechanical movement converter, the mechanical movement converter comprising a connecting rod operably coupled with a drive rotor wherein the drive rotor is operably coupled with the mechanical energy reservoir and the connecting rod is operably couplable with the lancet, a rotating movement of the drive rotor being transmitted through the connecting rod and converted into a linear movement of the lancet, wherein a rotation movement of the drive rotor in one direction is transmitted to charge the mechanical energy reservoir and a rotation movement of the drive rotor in the other direction is transmitted by the connecting rod to the lancet to execute the puncturing movement.

19. The system of claim 18, further comprising a motor for charging the mechanical energy reservoir.

20. The system of claim 18, wherein the movement converter or the motor is connected to a further system function which is independent of the mechanical energy reservoir.

21. The system of claim 20, wherein the system function independent of the mechanical energy reservoir comprises at least one function from the following group: execution of a sample recovery movement of a test element, transporting of an analytical aid comprising the lancet, transporting of a test element, and transporting of a test element magazine.

22. The system of claim 20, wherein the independent system function is actuated at the same time as the charging of the mechanical energy reservoir.

23. A method for collecting a liquid sample in a sample-collecting system having a housing by means of at least one analytical aid, the analytical aid comprising a lancet and a test element, the lancet and the test element being disposed on a support, and the test element having a test field for analysis of the liquid sample, the method comprising the following steps:
connecting a coupling element of the system to the lancet when the support of the analytical aid is positioned in a first position;
moving the coupling element with a drive unit from a rest position to a deployed position when the coupling element is coupled to the lancet with the support of the analytical aid in the first position to thereby move the lancet in a puncturing movement;
moving the support of the analytical aid relative to the coupling element from the first position to a second position and then connecting the coupling element to the test element when the support of the analytical aid is positioned in the second position; and
moving the coupling element with the drive unit from the rest position to the deployed position when the coupling element is coupled to the test element to thereby execute a sample recovery movement.

24. The method of claim 23, wherein the moving of the coupling element with the drive unit comprises moving the coupling element to move the lancet in the puncturing movement and then moving the coupling element to move the test element to execute the sample recovery movement.

25. The method of claim 23, further comprising:
recovering the liquid sample onto the analytical aid by driving the coupling element connected to the test element in order to execute the sample recovery movement; and
at the same time charging a mechanical energy reservoir with energy to drive a puncturing movement of the lancet connected to the coupling element;
wherein the coupling element is connected successively to the lancet and to the test element, further wherein the coupling element is moved from a rest position to a deployed position and back to the rest position in both the puncturing movement and in the sample recovery movement.

26. A method for collecting a liquid sample in a sample-collecting system having a housing by means of an analytical aid, the analytical aid comprising a lancet and a test element wherein the lancet and the test element are disposed on a support, the method comprising connecting a coupling member with the lancet and outputting energy from a mechanical energy reservoir to the coupling member through a transmission to drive the lancet in a puncture movement; moving the support of the analytical aid relative to the coupling member and connecting the coupling member to the test element and then moving the transmission to charge the mechanical energy reservoir with energy in order to drive a subsequent puncturing movement and wherein movement of the transmission simultaneously moves the test element in a sample recovery movement.

27. The method of claim 26, further comprising:
driving a coupling element connected to the test element in order to execute a sample recovery movement and thereby recovering a liquid sample; and
at the same time charging a mechanical energy reservoir with energy to drive a puncturing movement of the lancet connected to the coupling element;
wherein the coupling element is connected successively to the lancet and to the test element, further wherein the coupling element is moved from a rest position to a deployed position and back to the rest position in both the puncturing movement and in the sample recovery movement.

28. A method of executing a puncturing movement, the method comprising:
providing a housing with a drive unit couplable with a lancet, wherein the drive unit comprises a mechanical energy reservoir and a mechanical movement converter, the mechanical movement converter comprising a drive rotor operably couplable with the mechanical energy reservoir and operably couplable with a connecting rod;
rotating the drive rotor in a first rotational direction to charge the mechanical energy reservoir; and
after charging the mechanical energy reservoir, releasing stored energy from the mechanical energy reservoir to rotate the drive rotor in a second rotational direction opposite the first rotational direction to thereby impart motion to the connecting rod while the connecting rod is operably coupled with the lancet, the connecting rod converting the rotational movement of the drive rotor in the second rotational direction into linear movement of the lancet to thereby execute a puncturing movement.

29. The method of claim 28 wherein the lancet is provided as a part of an analytical aid wherein the analytical aid further comprises a test element and wherein the method further comprises:
uncoupling the lancet from the connecting rod after completing the puncture movement;
moving the analytical aid relative to the housing after uncoupling the lancet from the connecting rod;
rotating the drive rotor in the first direction to recharge the mechanical energy reservoir and simultaneously transmit movement to the connecting rod;
operably coupling the connecting rod with the test element as the drive rotor is rotated in the second rotational direction and using the connecting rod to convert the rotational movement of the drive rotor in the second rotational direction to linear movement of the test element and thereby execute a sample recovery movement.

30. The system of claim 18 wherein the mechanical movement converter is configured to couple with a test element when the drive rotor is rotated in the one direction to charge the mechanical energy reservoir and thereby convert rotational movement of the drive rotor in the one direction to linear movement of the test element and execute a sample recovery movement.

* * * * *